United States Patent [19]

Röhrscheid

[11] Patent Number: 4,748,278

[45] Date of Patent: May 31, 1988

[54] PROCESS FOR THE ISOLATION OF P-HYDROXYBENZALDEHYDE

[75] Inventor: Freimund Röhrscheid, Kelkheim, Fed. Rep. of Germany

[73] Assignee: Hoechst Aktiengesellschaft, Frankfurt am Main, Fed. Rep. of Germany

[21] Appl. No.: 886,973

[22] Filed: Jul. 17, 1986

[30] Foreign Application Priority Data

Jul. 19, 1985 [DE] Fed. Rep. of Germany ....... 3525848

[51] Int. Cl.$^4$ ...................... C07C 45/78; C07C 45/81
[52] U.S. Cl. ..................................... 568/438; 568/432
[58] Field of Search .............................. 568/438, 432

[56] References Cited

U.S. PATENT DOCUMENTS

| | | | |
|---|---|---|---|
| 3,098,875 | 7/1963 | Schmerling | 568/438 |
| 4,379,026 | 4/1983 | Jongsma | 568/438 |
| 4,453,016 | 6/1984 | Au et al. | 568/432 |
| 4,471,140 | 9/1984 | Au | 568/432 |

FOREIGN PATENT DOCUMENTS 0012939  1/1983  European Pat. Off.

Primary Examiner—Werren B. Lone
Assistant Examiner—Vera C. Clarke
Attorney, Agent, or Firm—Curtis, Morris & Safford

[57] ABSTRACT

The invention relates to a process for the isolation of p-hydroxybenzaldehyde from the reaction mixture obtained by oxidizing p-cresol with oxygen or oxygen-containing gases in methanol in the presence of Na or K hydroxide and an Mn, Ni, Cr or Co salt. The procedure in this process is optionally to add water to the reaction mixture, to heat the resulting solution and to filter off the precipitated Mn, Ni, Cr or Co oxide-hydrate, to remove the methanol from the filtrate by distillation, to cool the residual aqueous solution and thus to allow the p-hydroxybenzaldehyde to crystallize out in the form of the Na or K salt.

Alternatively, the reaction mixture is first dried by atomization, the soluble constituents of the dry substance are then dissolved in hot water, the undissolved Mn, Ni, Cr or Co oxide-hydrate is filtered off and the salt of p-hydroxybenzaldehyde is again allowed to crystallize out by cooling the filtrate.

A further method consists in diluting the reaction mixture with methanol, filtering off the undissolved Mn, Ni, Cr or Co oxide-hydrate, drying the filtrate by atomization, dissolving the resulting dry substance in hot water, and again allowing the p-hydroxybenzaldehyde to crystallize out as the Na or K salt by cooling the solution.

2 Claims, No Drawings

PROCESS FOR THE ISOLATION OF P-HYDROXYBENZALDEHYDE

The invention relates to the isolation of p-hydroxybenzaldehyde from the reaction mixture obtained by oxidizing p-cresol with oxygen. p-Hydroxybenzaldehyde and its derivatives are used as intermediate products in the preparation of dyestuffs, pharmaceuticals, plant protection agents and polymer resins.

Processes in which p-cresol is oxidized with molecular oxygen in the presence of Na or K hydroxide and a Co, Mn, Cr or Ni compound to give the alkali metal salt of p-hydroxybenzaldehyde are described in European Pat. No. 0,012,939, U.S. Pat. No. 4,453,016 and U.S. Pat. No. 4,471,140.

A particularly advantageous embodiment is the use of methanol as the solvent and of a Co salt as the catalyst. When the reaction is complete, the sodium or potassium salt of p-hydroxybenzaldehyde is present, partly in the form of a suspension, in methanol, together with a sludge of Co, Ni, Cr or Mn oxide-hydrate and dissolved alkali metal hydroxide. No technically utilizable solution is offered in the publications mentioned above to the problem of isolating the p-hydroxybenzaldehyde quantitatively, in a pure form, from this mixture.

It is suggested in European Pat. No. 0,012,939, page 4, line 40 that the product should be isolated by concentrating the reaction mixture by evaporating off the methanol, adding water to the concentrate, acidifying the mixture and extracting the desired aldehyde by means of an organic solvent. However, this procedure is associated with considerable difficulties:

(a) when the methanol is evaporated off, solid crusts are deposited on the reactor wall and block the stirrer and impede the flow of heat. As a result, only incomplete recovery of the methanol is possible and the rock-like crusts can only be dissolved in water with difficulty.

(b) When the concentrate to which water has been added is acidified, the p-hydroxybenzaldehyde is obtained in the form of a brown, tacky mass containing by-products and unreacted p-cresol. Since p-hydroxybenzaldehyde cannot be distilled without decomposition, even under vacuum, it has to be purified laboriously by recrystallization, in Example 1 of U.S. Pat. No. 4,471,140 from a mixture of chloroform and hexane.

(c) When the p-hydroxybenzaldehyde is liberated by means of acid, the metal catalyst dissolves as the salt and must subsequently be removed from the effluent.

Processes have now been found which avoid the problems described above and which make it possible to isolate, almost quantitatively and in high purity, the hydroxybenzaldehyde formed.

The invention relates firstly to a process for the isolation of p-hydroxybenzaldehyde from the reaction mixture obtained by oxidizing p-cresol with oxygen or oxygen-containing gases in methanol in the presence of Na or K hydroxide and an Mn, Ni, Cr or Co salt, which comprises adding water to the reaction mixture, heating the resulting solution and filtering off the precipitated Mn, Ni, Cr or Co oxide-hydrate, removing the methanol from the filtrate by distillation, cooling the residual aqueous solution and thus allowing the p-hydroxybenzaldehyde to crystallize out as the Na or K salt.

In general, 2 to 6, preferably 2.5 to 4, parts by weight of water per part by weight of p-cresol employed in the oxidation are added to the reaction mixture in this process, and the resulting solution is heated to about 50°–90° C. This mixture, in which the Na or K salt of p-hydroxybenzaldehyde is, surprisingly, particularly readily soluble, is filtered while hot in order to remove the precipitated oxide-hydrate. As a result, the latter does not reach the effluent and can be re-employed as a catalyst. The methanol is then removed by distillation from the orange-colored filtrate in a distillation column. Since methanol does not form an azeotrope with water, the methanol can thus be removed in an anhydrous form and used for a further reaction. The aqueous solution from the bottom of the column is cooled with stirring, preferably to approx. 5°. The sodium salt of p-hydroxybenzaldehyde, of the formula $Na(O.C_6H_4.CHO).2H_2O$, crystallizes out in the form of leaflets, whereas the potassium salt crystallizes with one molecule of water of hydration. Both can be filtered off easily.

The working up of the mother liquor described in the example shows that 98% of the p-hydroxybenzaldehyde formed has been precipitated as the sodium salt in the procedure described.

The invention also relates to a process for the isolation of p-hydroxybenzaldehyde from the reaction mixture obtained by oxidizing p-cresol by means of oxygen or oxygen-containing gases in methanol in the presence of Na or K hydroxide and an Mn, Ni, Cr or Co salt, which comprises drying the reaction mixture by atomization, dissolving the soluble constituents of the dry substance in hot water, filtering off the Mn, Ni, Cr or Co oxide-hydrate, which is undissolved thereby, and allowing the p-hydroxybenzaldehyde to crystallize out as the Na or K salt by cooling the filtrate.

The amount of water and its temperature and the temperature of crystallizing out are again as in the case of the process variant described above.

The invention also relates to a process for the isolation of p-hydroxybenzaldehyde from the reaction mixture obtained by oxidizing p-cresol by means of oxygen or oxygen-containing gases in methanol in the presence of Na or K hydroxide and an Mn, Ni, Cr or Co salt, which comprises diluting the reaction mixture with methanol, filtering off the undissolved Mn, Ni, Cr or Co oxide-hydrate, drying the filtrate by atomization, dissolving the resulting dry substance in hot water and allowing the p-hydroxybenzaldehyde to crystallize out as the Na or K salt by cooling the solution.

The amount of methanol employed for dilution is preferably about 0.2 to 1 part of methanol per part of reaction mixture. The amount of water and its temperature and also the temperature of crystallizing out are again as in the two process variants described above.

The solubility of the Na or K salt of p-hydroxybenzaldehyde is considerably reduced by adding the appropriate alkali metal ions, for example in the form of the hydroxides or halides. It is therefore possible, for example, to wash the crystals of the sodium salt which have been filtered off with a solution of sodium chloride without appreciable loss.

The sodium or potassium salt of p-hydroxybenzaldehyde which is isolated in accordance with the invention is a form of p-hydroxybenzaldehyde which is particularly advantageous for subsequent reactions; the salt can, for example, be employed without further treatment for reaction with dimethyl sulfate to give anisaldehyde.

If desired, however, it is readily possible to liberate p-hydroxybenzaldehyde from the alkali metal salt by the addition of acids. Its purity is over 99.5%.

It is preferable to oxidize p-cresol in the presence of sodium hydroxide, since the sodium salt of p-hydroxybenzaldehyde which is then formed is particularly sparingly soluble in cold water.

EXAMPLE

A solution of 432.6 g (4 mol) of p-cresol, 480 g (12 mol) of solid sodium hydroxide, 9.52 g (0.04 mol) of $CoCl_2 \cdot 6H_2O$ and 1000 g (1.26 liter) of methanol was oxidized with oxygen under normal pressure in a 4 liter flask equipped with a gas inlet tube, a thermometer, a reflux condenser and an impeller stirrer, at 60° C. and 800 revolutions/minute. The oxidation was discontinued after 11 hours; the consumption of $O_2$ was approx. 90 liter, corresponding to 100% of the theoretical requirement. The % conversion of the p-cresol was 93.1.

Working up:

The oxidized solution was mixed with 1200 g of water and heated to 70°. It was then filtered at 50°-60° through a heated filter in order to remove the precipitated cobalt oxide-hydrate. The methanol (99.9% pure) was removed by distillation from the orange-colored solution on a column (1.20 m; glass rings 4×4 mm). The methanol passed over at 35.5° C./260 mbar; the temperature of the bottom product rose from 53 to 73° C.

The aqueous solution remaining after the methanol had been distilled off was cooled to 5°, whereupon the sodium salt of p-hydroxybenzaldehyde crystallized out in the form of leaflets. The crystals were thoroughly suction-drained and washed with a little sodium hydroxide solution. The nearly colorless sodium salt of p-hydroxybenzaldehyde was dried.

In order to liberate the p-hydroxybenzaldehyde, the sodium salt in 1000 g of water was heated to 60° and then reacted with 200 ml of concentrated hydrochloric acid. The colorless p-hydroxybenzaldehyde was filtered off with suction, after cooling, and washed with three times 100 ml of water and dried at 40° C./33 mbar. Yield 289.8 g (=59.4% of theory, selectivity of conversion 63.8%), melting point 116°, purity 99.8%.

Working up the mother liquor:

The alkaline mother liquor obtained after the removal of the sodium salt of p-hydroxybenzaldehyde was acidified to pH 3. An oily substance was deposited and was extracted with 3×250 ml of ethyl acetate. The ethyl acetate was removed by distillation through a column, and the composition of the residue was examined by gas chromatography; it contained:

29.8 g of p-cresol (6.9%)

5.2 g of p-hydroxybenzaldehyde (1.1% of theory) and 24.6 g of p-hydroxybenzyl methyl ether (4.5% of theory).

Working up the mother liquor shows that the removal, according to the invention, of the sodium salt of p-hydroxybenzaldehyde is effected virtually quantitatively.

I claim:

1. A process for the isolation of p-hydroxybenzaldehyde from the reaction mixture obtained by oxidizing p-cresol with oxygen or oxygen-containing gases in methanol in the presence of Na or K hydroxide and an Mn, Ni, Cr or Co salt, which comprises adding 2 to 6 parts by weight of water per part by weight of p-cresol to the reaction mixture, heating the resulting solution to 50°-90° C. and filtering off the precipitated Mn, Ni, Cr or Co oxide-hydrate, removing the methanol from the filtrate by distillation, cooling the residual aqueous solution and thus allowing the p-hydroxybenzaldehyde to crystallize out in the form of the Na or K salt.

2. The process as claimed in claim 1, wherein 2.5 to 4 parts by weight of water per part by weight of p-cresol employed in the oxidation is added to the reaction mixture.

* * * * *